Figure 1:
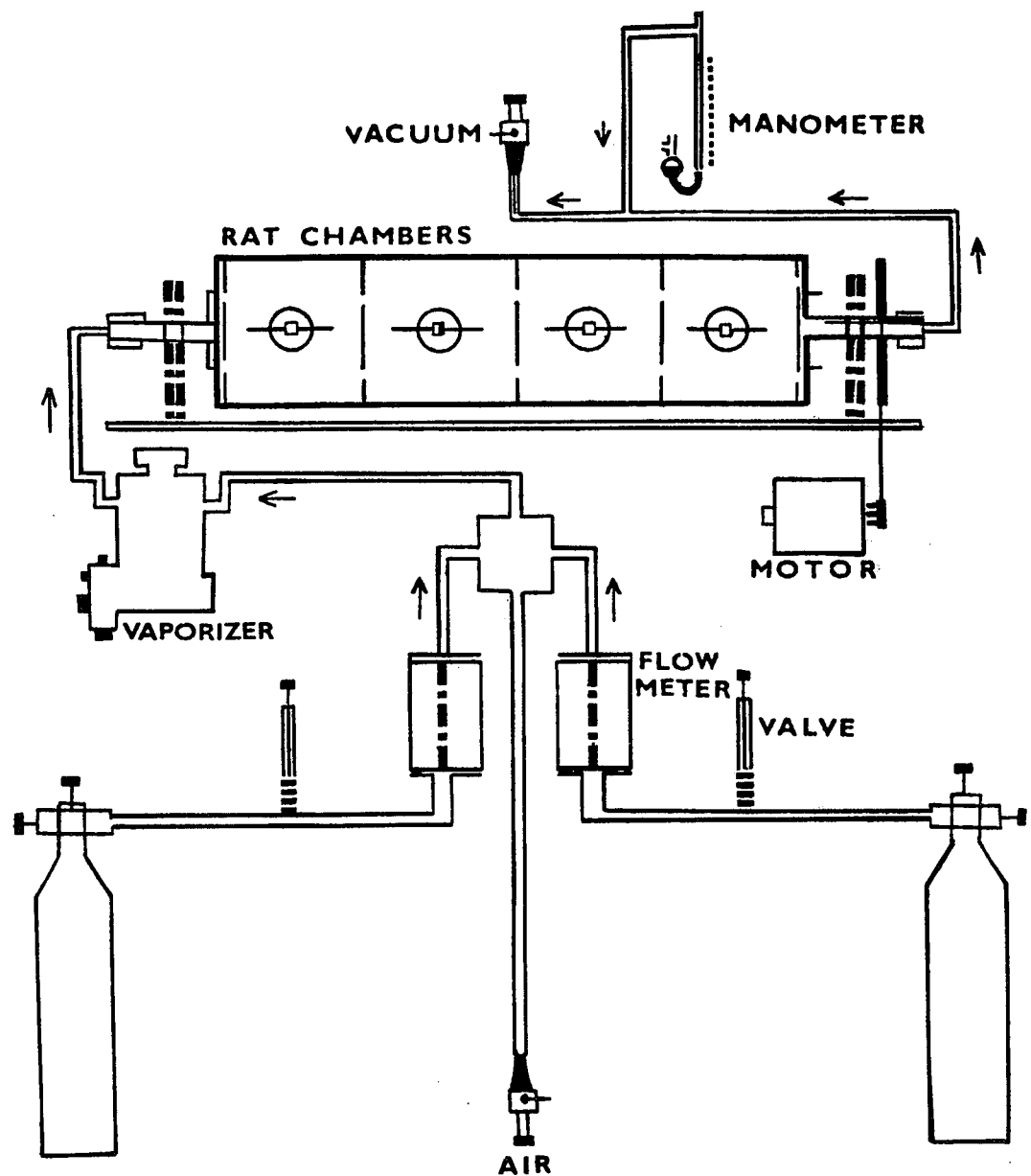

United States Patent [19]
Jaramillo

[11] 4,053,604
[45] Oct. 11, 1977

[54] METHOD FOR IMPROVING ANESTHESIA AND COMPOSITIONS THEREFOR

[75] Inventor: Jorge Jaramillo, Dollard des Ormeaux, Canada

[73] Assignee: Ayerst, McKenna & Harrison Limited, Montreal, Canada

[21] Appl. No.: 635,540

[22] Filed: Nov. 26, 1975

[51] Int. Cl.² .................. A61K 31/47; A61K 31/535; A61K 31/02

[52] U.S. Cl. .............. 424/258; 424/248.54; 424/254; 424/260; 424/350

[58] Field of Search ............... 424/258, 254, 260, 248

[56] References Cited

U.S. PATENT DOCUMENTS 3,852,452  12/1974  Bruderlein .................. 424/258
3,914,305  10/1975  Bruderlein et al. .......... 424/258

OTHER PUBLICATIONS

Janssen — J.A.C.S. vol. 78 (1956), p. 3862.

*Primary Examiner*—Sam Rosen
*Attorney, Agent, or Firm*—Arthur E. Wilfond

[57] ABSTRACT

Disclosed are methods and compositions for the prevention of painful conditions in an animal subject comprising the use of (+)(4a,13b-trans)-(3-hydroxy,13b-trans)-3-isopropyl-2,3,4,4a,8,9,13b,14-octahydro-1H-benzo[6,7]cyclohepta[1,2,3-de]pyrido[2,1-a]isoquinolin-3-ol, or a therapeutically acceptable acid addition salt thereof, alone or in a potentiating amount in combination with a suitable analgesic agent.

14 Claims, 5 Drawing Figures

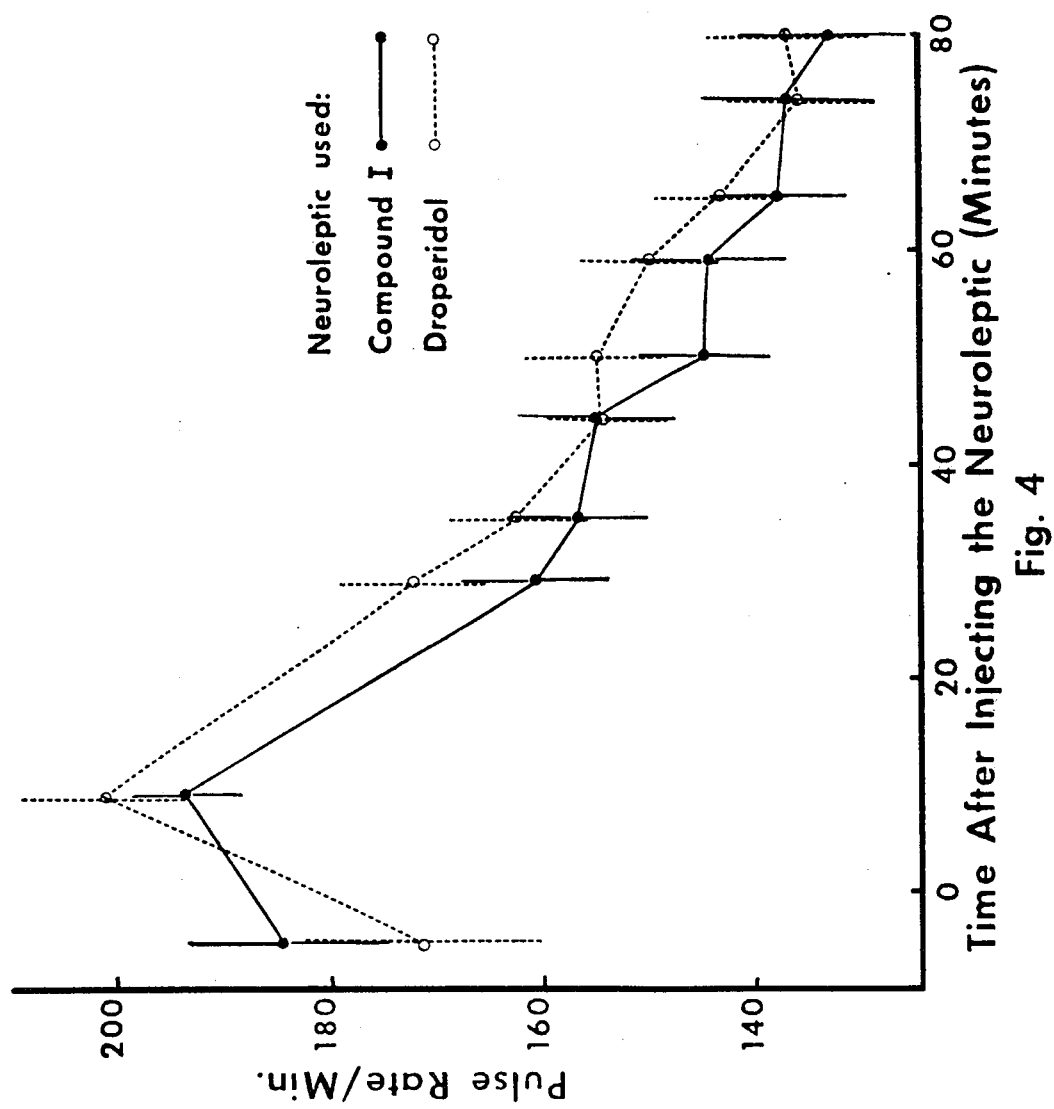

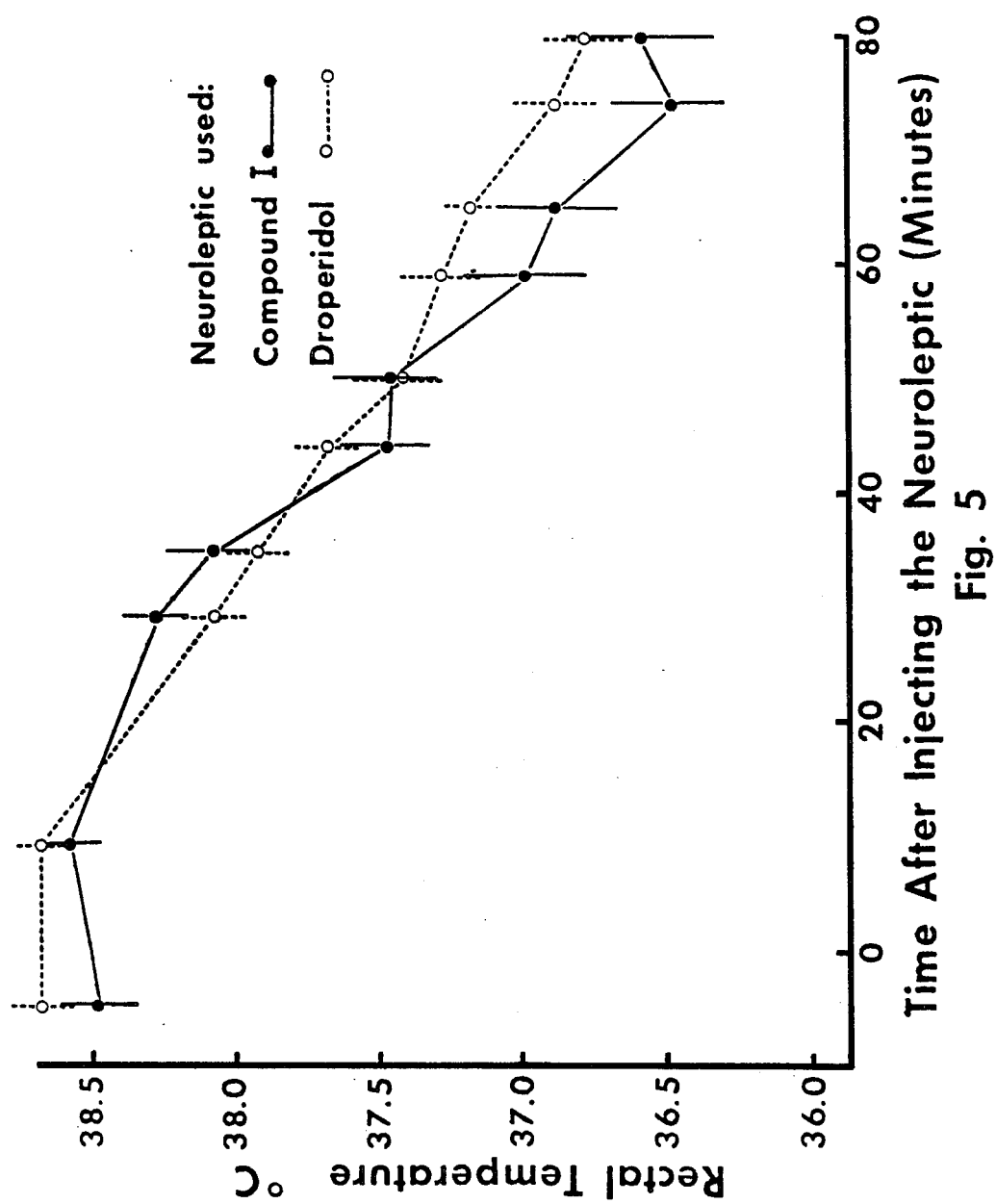

METHOD FOR IMPROVING ANESTHESIA AND COMPOSITIONS THEREFOR

BACKGROUND OF THE INVENTION a. Field of Invention

This invention relates to methods and compositions for improving anesthesia.

b. Prior Art

Anesthesia is generally looked upon as being composed of analgesia, unconciousness, depression or abolition of reflex activity and muscle relaxation. Neuroleptanalgesia (NLA), produced by the administration of a potent analgesic and a potent neuroleptic, is accepted as a fully adequate replacement for orthodox general anesthesia. Unlike orthodox general anesthesia, with the NLA method each of the elements — analgesia, neurolepsy and muscle relaxation — may be controlled separately and adapted to the needs of the individual patient, especially as far as degree and duration of activity are concerned. The emphasis in NLA is on the analgesic state provided by the narcotic analgesic and potentiated and improved by the psychic indifference and lack of initiative induced by the neuroleptic. When used in a suitable combination, these two drugs — the neuroleptic and the analgesic — can produce what has been called the neuroleptanalgesic state. In such a state, patients can undergo most surgical procedures. Since a minimum of noxious substances are administered, these patients emerge from such procedures with no significant metabolic derangement and with a reduced risk of serious complications.

General anesthesia, as obtained with the inhalation anesthetics or intravenous barbiturates, influences cell metabolism extensively, resulting in metabolic acidosis. Oxidative processes are depressed while intermediate metabolic reactions are more pronounced. On the other hand, the very slight degree of central depression and metabolic alteration, together with the low toxicity and stable circulation, makes the NLA procedure nearly ideal for poor risk and geriatric patients. The psychic indifference obtained with the NLA combination puts considerably less stress on the patient than complete unconsciousness. Since the NLA procedure is specially applicable to the elderly and poor risk patient, it would seem reasonable to extend this application to the normal healthy patient.

NLA has been called "balanced anesthesia" and can be defined as the use of drugs with highly specific action to achieve certain results necessary in order that a patient will tolerate a surgical or diagnostic procedure.

An important application of NLA is its use as a supplement to light general anesthesia; e.g., nitrous oxide, halothane. In this connection, the term "neuroleptanesthesia" was proposed by F. F. Foldes, et al., Anesth. Analg., 45, 642(1966) to characterize the state of patients receiving a neuroleptic, a narcotic analgesic and a general anesthetic, so that they become analgetic, sedated and anesthetized. It was further suggested by the investigators that the term neuroleptanalgesia be restricted to patients given neuroleptic and narcotic analgesic agents who became analgetic, sedated and amnesic — but are capable of obeying commands during surgery.

Moreover, it is now clear that in certain surgical and diagnostic procedures the NLA combination along provides as satisfactory anesthesia as any other method and is considered by many to be superior.

On the other hand, only a few methods and preparations are available for NLA, see for example, U.S. Pat. No. 3,141,823, issued July 21, 1964 and U.S. Pat. No. 3,662,073 issued May 9, 1972, and only one pharmaceutical composition, droperidolfentanyl, the subject matter of the former patent, is used to any degree in the field of anesthesia. Furthermore, not all combinations of known neuroleptic agents and analgesic agents are capable of producing neuroleptanalgesia. Accordingly, the search for improved methods and compositions for NLA goes on.

In this respect the present disclosure describes a novel method and compositions for effecting anesthesia. The method and compositions are applicable to NLA and have the attribute of improved safety features such as significantly less disturbances of the cardiovascular system.

SUMMARY OF THE INVENTION

One aspect of this invention involves a method for preventing painful conditions and providing psychic indifference to pain and stress in an animal subject, comprising:

administering concomitantly or sequentially to said subject a neuroleptanalgesically effective dose comprising (+)(4a,13b-trans)-(3-hydroxy,13b -trans)-3-isopropyl-2,3,4,4a, 8,9,13b, 14-octahydro-lH-benzo[6,7]cyclohepta[1,2,3-de]pyrido[2,1-a]isoquinolin-3-ol, or a therapeutically acceptable acid addition salt thereof, and a therapeutically acceptable analgesic agent or a therapeutically acceptable acid addition salt thereof, in a ratio ranging from 1:1 to 1000:1 on a weight to weight basis, respectively.

In another aspect of this invention, the latter method is followed five minutes to four hours thereafter by the administration to said subject of an anesthetically effective dose of a general anesthetic; said latter dose being substantially less than the anesthetically effective dose of the general anesthetic when given along for the same purpose.

Still another aspect of this invention relates to a pharmaceutical composition comprising (+)(4a,13b-trans)-(3-hydroxy,13b-trans)-3-isopropyl-2,3,4,4a,8,9,13b, 14-octahydro-lH-benzo[6,7]cyclohepta[1,2,3-de]-pyrido]2,1-a]isoquinolin-3-ol, or a therapeutically acceptable acid addition salt thereof, and a therapeutically acceptable analgesic agent or a therapeutically acceptable acid addition salt thereof, in a ratio ranging from 1:1 to 1000:1 on a weight to weight basis, respectively, and a pharmaceutically acceptable carrier.

Another aspect of this invention includes a method for preventing painful conditions and providing psychic indifference to pain and stress in an animal subject, comprising:

administering parenterally to said subject 10 to 250 µg/kg of a neuroleptically effective dose of (+)(4a,13b-trans)-(3-hydroxy,13b-trans)-3-isopropyl-2,3,4,4a,8,9,13b-14-octahydro-lH-benzo[6,7]cyclohepta(1,2,3-de)pyrido[2,1-a]isoquinolin-3-ol, or a therapeutically acceptable acid addition salt thereof.

In still another aspect of this invention, the latter method is followed 5 minutes to four hours thereafter by the administration to said subject of an anesthetically effective dose of a general anesthetic, said latter dose being substantially less than the anesthetically effective dose of the general anesthetic when given alone.

DETAILS OF THE INVENTION (+)(4a,13b-trans)-(3-hydroxy,13b-trans)-3-isopropyl-2,- 3,4,4a,8,9,13b,14-octahydro-1H-benzo[6,7]cyclohepta[1,2,3-de]pyrido[2,1-a]isoquinolin-3-ol, generically known as "dexclamol" and hereinafter referred to as Compound I, is a potent neuroleptic agent. The neuroleptic properties of the compound and of its salts are demonstrated readily in laboratory tests, such as those described by K. Voith and F. Herr, Psychopharmacologia (Berl.),42, 11(1975).

The preparation of the racemic mixture containing Compound I is described in U.S. Pat. No. 3,914,305, issued Oct. 21, 1975 and U.S. Pat. No. 3,852,452, issued Dec. 3, 1974. In these patents the racemic mixture is designated as "5-isopropyl-1,4,5,6,6a,10,11,15b-octahydro-3H-benzo[6,7]cyclohepta[1,2,3-de]pyrido[2,1-a]isoquinolin5-ol (Isomer A)." The separation of this racemate into its (+) and (−) isomers is accomplished by the use of d-tartaric acid. The (+) isomer (free base, i.e. Compound I) has $[\alpha]_D$ +215.8° (MeOH) and its corresponding hydrochloride salt has m.p. 260°–264° C and its corresponding hydrobromide has m.p. 265°–267°C.

Suitable analgesic agents for the practice of the present invention include the following examples:

fentanyl, N-(1-phenethyl-4-piperidyl)propionanilide, U.S. Pat. No. 3,141,823, meperidine, N-methyl-4-phenyl-4-carbethoxypiperidine, E. E. Smissman and G. Hite, J. Am. Chem, Soc., 81, 1201 (1959), fentatienyl, (R 30730), Abstracts of the 6th International Congress of Pharmacology, Helsinki, Finland, July 20–25, 1975, p.47.

azidomorphine J. Knoll, et al., J. Pharm. Pharmacol., 25, 929(1973), phenoperidine, 1-(3-hydroxy-3-phenylpropyl)-4-phenylisonipecotic acid ethyl ester, P. A. Janssen and N. B. Eddy, J. Med. Pharm. Chem., 2, 31 (1960, dextropropoxyphene, α-d-4-dimethylamino-3-methyl-1,2-diphenyl-2-butanol propionate, A. Pohland and H. R. Sullivan, J. Am. Chem. Soc., 77, 3400 (1955), and dextromoramide, 1-(3-methyl-4-morpholino-2,2-diphenylbutyrl)pyrrolidine, P. A. Janssen, J. Am. Chem. Soc., 78, 3862 (1956).

The term "animal subject" as used herein includes mammalian subjects and specifically includes humans.

In the following experiments, phenoperidine and Compound I are used in the form of their hydrochloride salt and droperidol in the form of its free base in the presence of lactic acid for adjustment to pH to 3.4. Results are expressed on the basis of the form of the drug employed (i.e., free base or hydrochloride salt).

Compound I shows only a negligible amount of analgesic activity (see Table 1) but it exerts a well defined potentiating effect on analgesic agents. Evidence for this effect is demonstrated readily by the tail-flick test, F. E. D'Amour and D. L. Smith, J. Pharmacol., 72, 74 (1941), in experiments in which the analgesic agent is exemplified by phenoperidine.

Results of such tests using albino mice are illustrated by tables 1,2 and 3 in which the neuroleptic agent, droperidol, is included for comparative purposes.

TABLE 1

| Treatment | Analgesic Activity ($ED_{50}$) |
|---|---|
| | $ED_{50}$, mg/kg, i.p.* |
| phenoperidine | 0.50 ± 0.1 |
| Compound 1 | >35 |
| droperidol | >30 |

*The dose which increased analgesia by 50% when tested 15 minutes after drug administration.

TABLE 2

Potentiation of the Analgesic Activity ($ED_{50}$) of Phenoperidine, i.e. 0.5 mg/kg, by varying Doses of Neuroleptic Agents.

| Treatment | $PD_{50}$, mg/kg, i.p. of Neuroleptic Agent* |
|---|---|
| Compound 1 | 0.56 ± 0.06 |
| Droperidol | 0.55 ± 0.10 |

*$PD_{50}$ refers to the dose of the neuroleptic which increased the analgesic activity ($ED_{50}$) of phenoperidine by 50%.

TABLE 3

Modified Analgesic Activity of Phenoperidine in the Presence of the Neuroleptic $PD_{50}$.

| Treatment | $ED_{50}$, mg/kg i.p. of phenoperidine* |
|---|---|
| Compound 1 | 0.15 ± 0.07 |
| droperidol | 0.19 ± 0.05 |

*$ED_{50}$ refers to the analgesic activity of phenoperidine after pretreatment with a fixed dose ($PD_{50}$) of the neuroleptic agents.

The results illustrated by Tables 1,2 and 3 show that the analgesic activity of phenoperidine was significantly enhanced by the concomitant administration of Compound I or droperidol. In this respect Compound I and droperidol were equiactive. Note that no analgesic activity could be demonstrated for either Compound I or droperidol when given alone (Table 1).

With respect to the use of Compound I with general anesthetics, Compound I exerts a well defined potentiating effect on such anesthetic. When Compound I is administered to a subject prior to anesthetic treatment, the induction time for the anesthetic is substantially reduced. Noteworthy is the fact that this interaction occurs at doses of Compound I which are considerably less than the minimum effective dose of Compound I required for neuroleptic and associated effects, such as effects on normal posture or behavior.

This potentiating interaction of Compound I on induction time is demonstrated readily by the following testing procedure in which the general anesthetic is exemplified by halothane. (Similar results also are obtained using nitrous oxide or a mixture of halothane and nitrous oxide instead of halothane).

The effects of Compound I on halothane-induced anesthesia were assesses using 20 rats for each dose or time interval determination. The experiments were performed on male albino rats (Sprague-Dawley) weighing from 180–220 g. A schematic representation of the apparatus used is illustrated in FIG. 1. The apparatus consists of a rectangular box made of transparent plastic (115 cm long × 28 cm high × 28 cm wide) which is divided into 4 equal chambers by perforated walls. The box rotates around a hollow axis through which gases can be delivered at several proportions from cylinders, through their respective flowmeters. An in-line halothane vaporizer is placed just before the gases reach the chambers. There is an air-tight door to every chamber through which two animals, one treated and one control, are introduced. The gases are delivered at one end of the box and suction is applied to the other end to take up the gases after flowing through the chambers. An in-line water manometer monitors the resulting pressure. This pressure is kept at 0-5 mm $H_2O$ to make certain the gases in the anesthetic chambers remain at atmospheric pressure. The mixture of gases is delivered at a rate of 15 l/min. The inhalation anesthetic gases are delivered for ten minutes prior to the introduction of the animals into the chambers to assure an even distribution in the four chambers. The chambers rotate at four rev/min forcing the animals to tumble and allowing the experimenter to accurately time the loss and recovery of the righting reflex. Induction times are recorded as the time interval elapsed between the beginning of exposure of the animals to the gases and the amount in which they lose their righting reflex.

Groups of control animals (four at a time) were subjected to halothane concentrations ranging from 0.5 to 2.5% in a mixture of 95% $O_2$-5% $CO_2$, and the induction times thus obtained were used to calculate concentration-reponse curves. Since a certain time elapsed between putting the first and the last rat into their respective chambers, each animal was timed separately with a stopwatch. In control experiments with halothane alone, a 1% concentration was found to be an intermediate dose capable of achieving a well-defined and reproducible pharmacological effect (with this concentration all the animals lost their righting reflex in an average of 2.4 minutes). This intermediate concentration of halothane was then used to study the effects of increasing doses of the test compound on the induction times and anesthesia times.

The animals were pretreated by administering the test compounds in dosages ranging from 10 to 500 αg/kg, i.v., at 5, 30, 60, 120, 240 and 360 minutes prior to their exposure to halothane. As soon as all animals lost their righting reflex, the $O_2$-halothane flow was discontinued and replaced by an equal flow of air. The animals were allowed to remain in the rotating chambers until they regained their righting reflex. Anesthesia times were determined as the interval between the time required to lose and the time to regain the righting reflex. Air flushing of the anesthetic chambers was performed after each determination and the entire procedure repeated with another group of animals for the determination of the effect of a new dose or concentration.

Drugs used in this study include: droperidol, phenoperidine hydrochloride, halothane and Compound I in the form of its hydrochloride salt. Phenoperidine hydrochloride and Compound I (hydrochloride) were dissolved separately in a warm solution of 0.9% sodium chloride. Droperidol was suspended in saline with the aid of a drop ot Tween 80 (Tween 80 is a registered trademark for a complex mixture of polyoxyethylene ethers of mixed partial oleic esters of sorbitol anhydride). Dosages are expressed in this study as the salt form of the compound where appliable. When the experimental protocol called for the concomitant administration of two drugs, these were mixed in the syringe and administered intravenously. The drugs were injected in a volume of 0.1 ml/100 g body weight.

The statistical analysis of the data was performed using Student's $\pm$ test.

With reference to the effect of Compound I on the induction time of rats exposed to halothane anesthesia, the results are tabulated in Table 4.

TABLE 4.

Induction times $\pm$ S.D. (in min) observed in control animals and in those treated with increasing doses of compound 1, 5 min prior to their exposure to various concentrations of halothane.

| Compound 1 Dose μg/kg i.v. | Halothane Concentrations % | | | | | | | | | | | | | | |
|---|---|---|---|---|---|---|---|---|---|---|---|---|---|---|---|
| | 0.75 | | | 1.0 | | | 1.5 | | | 2.0 | | | 2.5 | | |
| | C | T | Sig. | C | T | Sig. | C | T | Sig. | C | T | Sig. | C | T | Sig. |
| 10 | 6.84 ± 0.20 | 6.66 ± 0.22 | N.S. | 2.75 ± 0.07 | 2.67 ± 0.12 | N.S. | 1.32 ± 0.04 | 1.32 ± 0.04 | N.S. | 0.73 ± 0.01 | 0.72 ± 0.01 | N.S. | 0.58 ± 0.01 | 0.57 ± 0.01 | N.S. |
| 25 | 6.57 ± 0.18 | 6.30 ± 0.19 | N.S. | 2.22 ± 0.06 | 1.86 ± 0.05 | *** | 1.05 ± 0.03 | 1.02 ± 0.02 | N.S. | 0.75 ± 0.01 | 0.71 ± 0.01 | ** | 0.62 ± 0.02 | 0.58 ± 0.02 | * |
| 50 | 7.05 ± 0.21 | 5.77 ± 0.17 | *** | 2.11 ± 0.05 | 1.62 ± 0.04 | *** | 1.14 ± 0.03 | 1.03 ± 0.02 | ** | 0.80 ± 0.01 | 0.75 ± 0.01 | * | 0.60 ± 0.01 | 0.57 ± 0.01 | N.S. |
| 100 | 6.98 ± 0.16 | 4.05 ± 0.15 | *** | 2.10 ± 0.07 | 1.37 ± 0.06 | *** | 1.28 ± 0.03 | 1.13 ± 0.02 | *** | 0.73 ± 0.01 | 0.69 ± 0.01 | * | 0.59 ± 0.01 | 0.54 ± 0.01 | ** |
| 200 | 6.70 ± 0.19 | 3.48 ± 0.13 | *** | 2.19 ± 0.05 | 1.31 ± 0.04 | *** | 1.35 ± 0.02 | 1.03 ± 0.02 | *** | 0.70 ± 0.02 | 0.64 ± 0.02 | ** | 0.62 ± 0.02 | 0.57 ± 0.02 | * |
| 250 | 5.87 ± 0.14 | 3.72 ± 0.08 | *** | 2.14 ± 0.06 | 1.67 ± 0.05 | *** | 1.10 ± 0.04 | 0.91 ± 0.01 | *** | 0.72 ± 0.02 | 0.67 ± 0.01 | * | 0.63 ± 0.01 | 0.60 ± 0.01 | * |

C = Control
T = Treated
N.S. = Not significant
* = p = 0.05
** = p = 0.01
*** = p = 0.001

Table 4 results show that Compound I (hydrochloride) decreased considerably the induction time of rats exposed to halothane anesthesia. The effect was more pronounced at the lower concentrations (0.75 -1%) than at the higher concentrations (2-14 2.5%) of halothane. It can be seen that Compound I (hydrochloride) in doses of 200 μg/kg, i.v., was sufficient to reduce by approximately 50% the induction time of rats subjected to a 1% halothane concentration.

With reference to the effect of Compound I on the anesthesia time of rats exposed to halothane anesthesia, the results are tabulated in Table 5.

TABLE 5

Anesthesia times ± S.D. (in min) recorded in control animals and in those treated with increasing doses of Compound 1, 5 min prior to their exposure to various concentrations of halothane.

| Compound 1 Dose µg/kg i.v. | Halothane Concentrations % | | | | | | | | | | | | | | |
|---|---|---|---|---|---|---|---|---|---|---|---|---|---|---|---|
| | 0.75 | | | 1.0 | | | 1.5 | | | 2.0 | | | 2.5 | | |
| | C | T | Sig. | C | T | Sig. | C | T | Sig. | C | T | Sig. | C | T | Sig. |
| 10 | 3.65 ± 0.15 | 3.67 ± 0.15 | N.S. | 3.12 ± 0.18 | 3.16 ± 0.19 | N.S. | 3.69 ± 0.21 | 3.84 ± 0.24 | N.S. | 4.54 ± 0.32 | 4.68 ± 0.35 | N.S. | 5.36 ± 0.37 | 5.42 ± 0.37 | N.S. |
| 25 | 3.44 ± 0.29 | 3.78 ± 0.26 | N.S. | 3.17 ± 0.16 | 3.62 ± 0.19 | N.S. | 4.34 ± 0.27 | 4.61 ± 0.26 | N.S. | 4.74 ± 0.32 | 5.09 ± 0.35 | N.S. | 5.01 ± 0.33 | 5.26 ± 0.35 | N.S. |
| 50 | 3.53 ± 0.30 | 5.16 ± 0.23 | *** | 3.52 ± 0.20 | 4.67 ± 0.26 | ** | 4.10 ± 0.29 | 4.59 ± 0.29 | N.S. | 4.29 ± 0.27 | 4.49 ± 0.27 | N.S. | 4.72 ± 0.31 | 4.96 ± 0.29 | N.S. |
| 100 | 2.75 ± 0.19 | 6.33 ± 0.20 | *** | 3.38 ± 0.18 | 5.34 ± 0.21 | *** | 3.89 ± 0.25 | 4.79 ± 0.28 | * | 4.71 ± 0.31 | 5.49 ± 0.37 | N.S. | 4.93 ± 0.31 | 5.62 ± 0.35 | N.S. |
| 200 | 3.00 ± 0.23 | 6.54 ± 0.17 | *** | 3.51 ± 0.19 | 5.37 ± 0.29 | *** | 3.77 ± 0.29 | 4.94 ± 0.29 | ** | 4.37 ± 0.30 | 5.33 ± 0.33 | * | 5.15 ± 0.33 | 5.89 ± 0.32 | N.S. |
| 250 | 3.59 ± 0.15 | 6.26 ± 0.18 | *** | 3.41 ± 0.15 | 5.81 ± 0.23 | *** | 4.36 ± 0.21 | 5.52 ± 0.28 | ** | 5.05 ± 0.36 | 5.92 ± 0.36 | N.S. | 5.38 ± 0.38 | 6.37 ± 0.44 | N.S. |
| 500 | — | — | — | 3.10 ± 0.17 | 5.69 ± 0.24 | *** | — | — | — | — | — | — | — | — | — |

C = Control
T = Treated
N.S. = Not significant
* = P = 0.05
** = P = 0.01
*** = P = 0.001

Table 5 results show that anesthesia time was increased considerably in animals treated with Compound 1 (hydrochloride). The maximum effect, as in the case of the induction time, was obtained in the animals receiving halothane concentrations of 0.75–1%. The anesthesia time was increased by approximately 70% five minutes after the intravenous administration of Compound 1 (hydrochloride) in rats exposed to 1% halothane.

With reference to the potentiation by an analgesic of the effects of Compound 1 on the induction time of rats exposed to halothane anesthesia, experiments were performed using a dose of the analgesic, e.g. phenoperidine hydrochloride at a dose of 25 µg/kg, i.v., which did not modify the induction nor the anesthesia time of rats anesthetized with halothane. The results of one such experiment, together with an experiment in which Compound 1 (hydrochloride) was given alone is depicted in FIG. 2.

Figure 2:
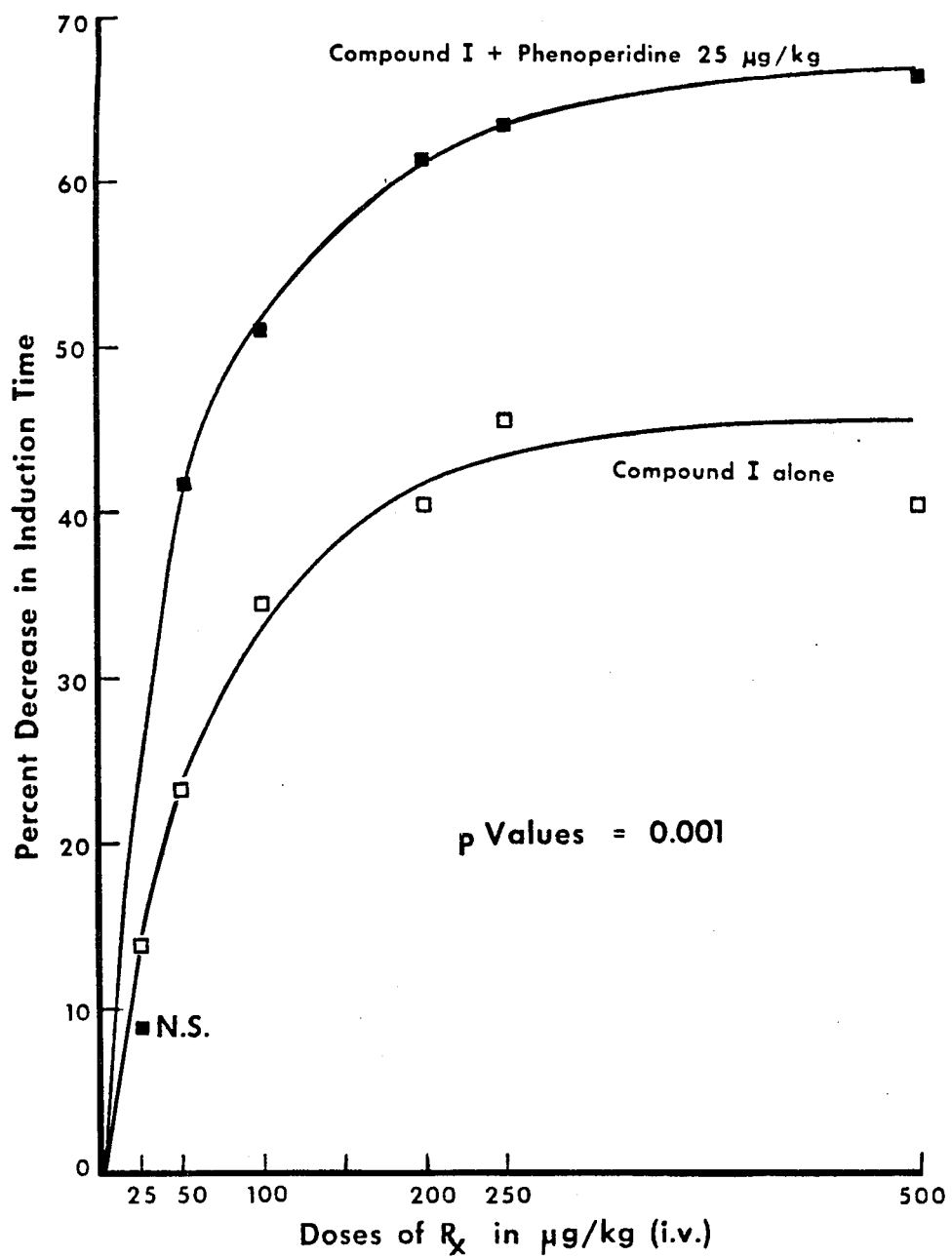

More specifically, FIG. 2 illustrates the effects of Compound 1 alone (lower curve) and in combination with 25 µg/kg, i.v. of phenoperidine hydrochloride (upper curve) on the induction time of rats exposed to 1% halothane. The animals received drug treatment 5 minutes prior to their exposure to anesthetic vapors. The abscissa represents the doses of Compound 1 in µg/kg, i.v.

In FIG. 2 the potentiating effect of phenoperidine hydrochloride on the effects of Compound 1 (hydrochloride) on rats receiving halothane is seen clearly. It is interesting to note here that a maximum of 45% decrease in induction time was achieved with a dose of Compound 1 (hydrochloride) alone, and the addition of 25 µg/kg, i.v., phenoperidine hydrochloride was sufficient to increase this activity to about 65%.

With reference to the potentiation by an analgesic on the effect of Compound 1 on the anesthesia time of rats exposed to halothane anesthesia, experiments also were performed with a dose of the analgesic that did not modify the induction nor the anesthesia time of rats anesthetized with halothane. The results of such an experiment are depicted in FIG. 3.

Figure 3:
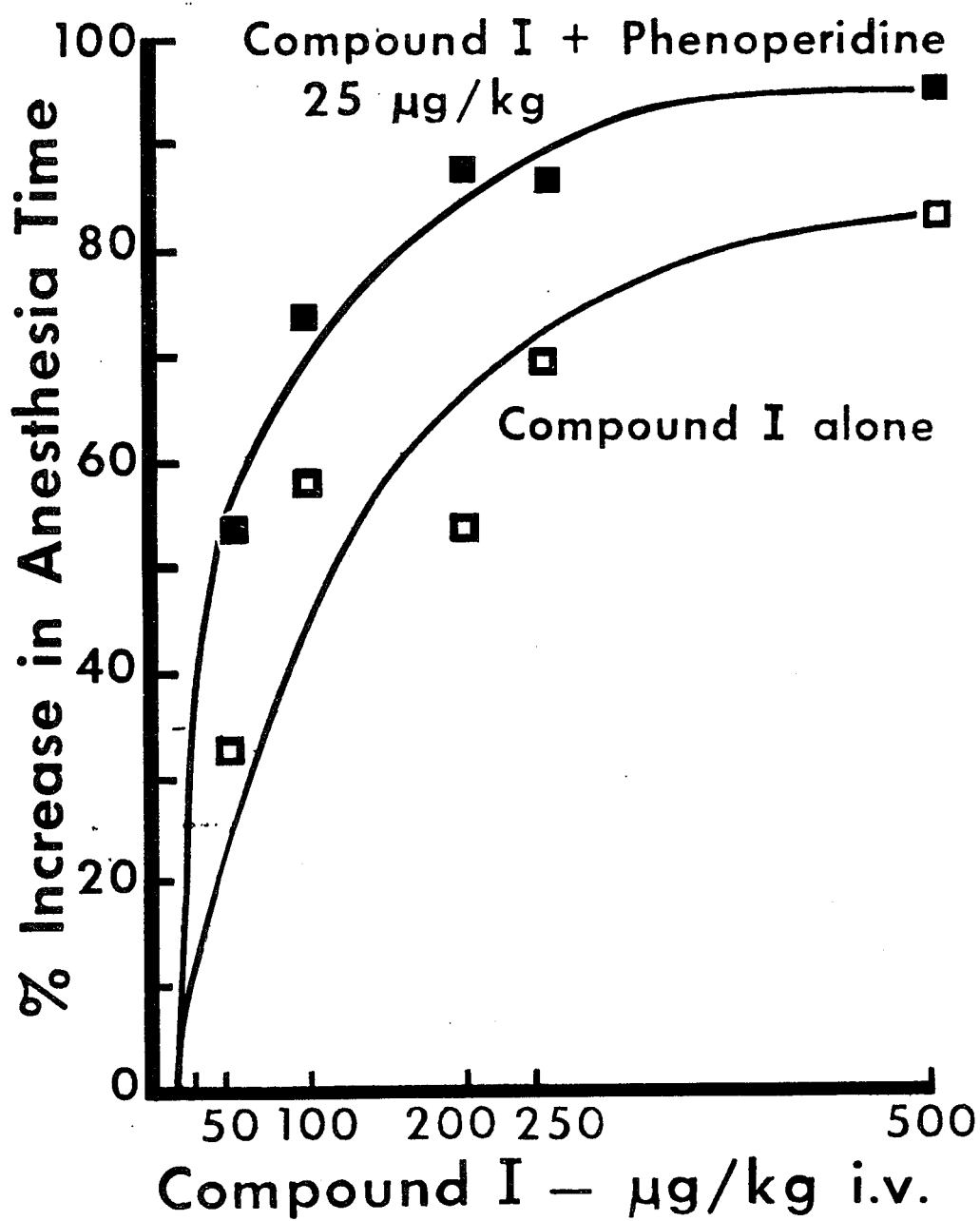

More specifically, FIG. 3 illustrates the effects of Compound 1 alone (lower curve) and in combination with 25 µg/kg, i.v. of phenoperidine hydrochloride (upper curve) on the anesthesia time of rats exposed to 1% halothane. The animals received drug treatment 5 minutes prior to their exposure to anesthetic vapors. The abscissa represents the doses of Compound 1 in µg/kg, i.v.

FIG. 3 clearly shows that the addition of the analgesic to Compound 1 (hydrochloride) potentiates the duration of anesthesia effect of the latter agent.

The interactions of Compound 1 with the effects of a general anesthetic also were assessed in a "double-blind" cross-over study in dogs, in which Compound 1 (hydrochloride) was compared to droperidol as the neuroleptic component of a neuroleptanalgesic combination. Nitrous oxide was used as the general anesthetic and fentanyl served as the narcotic analgesic. Neuroleptanesthesia was induced with a mixture of the neuroleptic, the analgesic and nitrous oxide-oxygen. The experimental protocol (Table 6) was designed to mimic in animals the procedure followed in the clinic when a neuroleptanalgesic combination is used in conjunction with general anesthesia.

TABLE 6

Protocol for Studying the Effects in Dogs of a Neuroleptic (Compound 1 or droperidol), an Analgesic (fentanyl) and an Anesthetic (nitrous oxide-oxygen)

| Time Min. | Drug Treatment or Procedure | Dose | Route of Administration |
|---|---|---|---|
| −30 | Diphenhydramine | 5 mg/kg | I.m. |
| −15 | Meperidine | 5 mg/kg | I.m. |
| −14 | Atropine | 50 µg/kg | I.m. |
| −5 | OBSERVATIONS | | |
| −4 | Insert i.v. catheter | | |
| 0 | Neuroleptic A or B* | 200 µg/kg | i.v. |
| 9 | OBSERVATIONS | | |
| 10 | Fentanyl | 5 µg/kg | i.v. |
| 12 | Fentanyl | 2 µg/kg | i.v. |
| 13 | N₂0-O₂ | 4:1 | mask |
| 15 | Fentanyl | 2 µg/kg | i.v. |

TABLE 6-continued
Protocol for Studying the Effects in Dogs of a Neuroleptic (Compound 1 or droperidol), an Analgesic (fentanyl) and an Anesthetic (nitrous oxide-oxygen)

| Time Min. | Drug Treatment or Procedure | Dose | Route of Administration |
|---|---|---|---|
| 20 | Lidocaine - intubation | | spray |
| 21 | $N_2O-O_2$ | 3:1 | trachea |
| 25 | Skin incision | | |
| 29 | OBSERVATIONS | | |
| 30 | Fentanyl** | 2 μg/kg | i.v. |
| 31 | $N_2O-O_2$ | 2:1 | |
| 35 | OBSERVATIONS | | |
| 44 | OBSERVATIONS | | |
| 45 | Fentanyl** | 2 μg/kg | i.v. |
| 50 | OBSERVATIONS | | |
| 59 | OBSERVATIONS | | |
| 60 | Fentanyl** | 2 μg/kg | i.v. |
| 65 | OBSERVATIONS | | |
| 70 | Skin incision | | |
| 74 | OBSERVATIONS | | |
| 75 | Fentanyl** | 2 μk/kg | i.v. |
| 80 | OBSERVATIONS | | |
| 90 | Turn off $N_2O-O_2$-extubation | | |

*Either Compound 1 or droperiodol
**When required

Compound 1 at a dose of 200 μg/kg intravenously was as effective as droperidol at the same dose in inducing neurolepsy and in supplementing nitrous oxide anesthesia (Table 7).

Changes in pulse rate, respiratory rate and rectal temperature in the animals treated with Compound 1 were not statistically different from those observed in the animals treated with droperidol, see FIGS. 4 and 5.

Turning now to safety features, with respect to respiratory minute volume and means arterial blood pressure effects, Compound 1 causes only a very small increase in minute volume and a minor diminution of blood pressure only at the upper level of the therapeutically effective neuroleptic dosages. These effects are less than those encountered with neuroleptics presently available for NLA as evidenced by laboratory experiments in rats in which these cardiovascular parameters are measured before and after the administration of Compound 1 and the neuroleptic agent droperidol, see Table 8.

TABLE 8
The Effect of Compound 1 and Droperidol on Respiratory Minute Volume and Mean Arterial Blood Pressure

| Treatment (μg/kg) | No. Rats | Minute Volume ml Before Drug | Change in Minute Volume as % of Control | Mean B.P. mm Hg Before Drug | Change in Mean B.P. as % of Control |
|---|---|---|---|---|---|
| Compound 1 | | | | | |
| 25 | 6 | 288.3 ± 16.7 | +4.2 ± 1.4* | 81.0 ± 7.1 | −0.83 ± 0.83N.S. |
| 100 | 6 | 253.3 ± 10.0 | +6.8 ± 1.9* | 91.3 ± 5.5 | −4.1 ± 2.6N.S. |
| 250 | 8 | 261.3 ± 21.2 | +6.6 ± 2.7N.S. | 70.8 ± 5.0 | −8.9 ± 1.6** |
| Droperidol | | | | | |
| 25 | 6 | 247.5 ± 28.2 | +13.9 ± 3.0* | 82.5 ± 5.4 | −28.4 ± 4.6** |
| 100 | 6 | 278.3 ± 19.2 | +15.6 ± 6.2* | 71.83 ± 6.8 | −15.4 ± 5.9N.S. |
| 250 | 6 | 293.3 ± 24.2 | +27.3 ± 8.1 | 90.0 ± 3.8 | −26.9 ± 3.2** |

*$P < 0.05$
**$P < 0.01$
N.S. not significant
{ Students '+' test for paired data.

Furthermore, in like experiments in which the rats were administered Compound 1 and an analgesic agent, for example, phenoperidine, it was demonstrated that the well known respiratory depression caused by analgesic agents, for example phenoperidine, is only slightly changed at doses substantially greater than those required for NLA when Compound 1 is used intravenously in combination with an analgesic agent.

The beneficial effects obtained by combining Compound 1 and an analgesic are demonstrated in the following experiment in which the behavioral changes and side effects elicited by Compound 1 were recorded in cebus monkeys when the drug was given alone and in combination with the analgesic phenoperidine.

In a first group of animals (Table 9), Compound 1 was effective in eliciting behavioral changes at very small

TABLE 7
Intubation, Extubation and Anesthesia Times in Dogs Under Neuroleptanesthesia

| | Intubation Time Min | | Extubation Time Min | | Duration of Anesthesia[b] Time Min | | Average Score[a] Neuroleptanesthesia | |
|---|---|---|---|---|---|---|---|---|
| Dog No. | Compound 1 | Droperidol | Compound 1 | Droperidol | Compound 1 | Droperidol | Compound 1 | Droperidol |
| 12 | 19 | 18 | 90 | 90 | 90 | 90 | 4.0 | 4.0 |
| 20 | 26 | 19 | 90 | 73 | 95 | 75 | 3.0 | 3.2 |
| 26 | 25 | 32 | 90 | 90 | 91 | 91 | 3.5 | 4.0 |
| 28 | 20 | 17 | 59 | 80 | 59 | 80 | 3.3 | 3.5 |
| 30 | 18 | 18 | 90 | 70 | 92 | 70 | 3.5 | 3.0 |
| 95 | 16 | 20 | 90 | 90 | 92 | 93 | 4.0 | 4.0 |
| 150 | 20 | 17 | 25 | 36 | 25 | 36 | 2.0 | 2.7 |
| 153 | | | | | | | 1.0 | 1.0 |
| 159 | | 30 | | 40 | | 40 | 1.0 | 2.0 |
| 160 | 20 | 18 | 90 | 49 | 93 | 49 | 4.0 | 3.2 |
| 162 | 26 | 29 | 54 | 90 | 54 | 90 | 3.0 | 3.2 |
| 163 | 23 | 21 | 90 | 90 | 90 | 92 | 4.0 | 3.7 |
| 710 | 18 | 19 | 50 | 72 | 50 | 72 | 3.2 | 3.2 |
| 171 | 20 | 17 | 90 | 90 | 90 | 90 | 5.0 | 4.5 |
| 173 | 17 | 20 | 90 | 90 | 91 | 92 | 4.0 | 4.8 |
| 174 | 20 | 18 | 80 | 90 | 80 | 93 | 2.8 | 3.8 |
| Average | 20.57 | 20.21 | 77.0 | 78.6 | 78.0 | 79.5 | 3.2 | 3.3 |
| ±S.E. | ±0.86 | ±1.22[n] | ±5.7 | ±4.6[n] | ±5.8 | ±4.8[n] | ±0.17 | ±0.15[n] |

[a] A cross-over design was used in assessing the effects of the narcotic, anesthetic and the 2 neuroleptics. At least 15 days elapsed before a dog was used for the second time. In the ratings, the higher the score the better the neuroleptanesthesia. The same investigators scored the degree of anesthesia in all of the animals without knowing which neuroleptic was administered (i.e., "double-blind").
[b] As measured by the time the animals regained their righting reflex.
[n] No significant difference from the values obtained with Compound 1.

doses. Signs of excitomotor agitation (extrapyramidal excitation) were observed in the monkeys only when the doses were increased several fold (50–100 mg/kg).

geously, the compound or the combination is given parenterally; however, the method of administering the present active ingredients of this invention is not to be

TABLE 9

Behavioral and Side Effects Elicited by the i.v. Administration of Compound 1 to Cebus Monkeys.

| Animal | Sex | Dose μg/kg | Behavioral Changes | Onset Min | Duration Hr | Side Effects |
|---|---|---|---|---|---|---|
| E | ♀ | 5 | None | — | — | None |
| F | ♀ | 5 | None | — | — | None |
| M | ♀ | 5 | None | — | — | None |
| N | ♀ | 5 | None | — | — | None |
| 1 | ♀ | 10 | Passive | 30 | 3 | None |
| 2 | ♀ | 10 | Huddle | 20 | 3 | None |
| 6 | ♀ | 10 | Passive | 15 | >4 | None |
| 8 | ♀ | 10 | Passive | 60 | 2 | None |
| 3 | ♀ | 20 | Huddle | 20 | 4 | None |
| 4 | ♀ | 20 | Huddle | 15 | >5 | None |
| 9 | ♀ | 20 | Passive | 15 | >5 | None |
| 10 | ♀ | 20 | Passive-Huddle | 20 | 3 | None |
| 5 | ♀ | 50 | Huddle | 20 | >4 | Extrapyramidal (30 min) |
| 7 | ♀ | 50 | Huddle | 10 | >4 | None |
| A | ♀ | 50 | Huddle | 20 | >4 | None |
| B | ♀ | 50 | Huddle | 20 | >4 | Extrapyramidal (40 min) |
| C | ♀ | 100 | Huddle | 10 | >24 | Extrapyramidal (15 min) |
| D | ♀ | 100 | Huddle | 5 | >24 | Extrapyramidal (15 min) |
| F | ♀ | 100 | Huddle | 10 | >24 | Extrapyramidal (10 min) |
| G | ♀ | 100 | Huddle | 5 | >24 | Extrapyramidal (10 min) |

Numbers in parenthesis indicate the time of onset of side effect indicated.

When phenoperidine was administered to a second group of animals (Table 10), undesirable side effects such as salivation and vomiting were consistently observed at the same doses (50–100 μg/kg) producing the main beneficial effect (sedation).

TABLE 10

Behavioral and Side Effects Elicited by the i.v. Administration of Phenoperidine to Cebus Monkeys.

| Animal | Sex | Dose μg/kg | Behavioral Changes | Onset Min | Duration Hr | Side Effects |
|---|---|---|---|---|---|---|
| E | ♀ | 10 | None | — | — | None |
| H | ♀ | 10 | None | — | — | None |
| A | ♀ | 10 | None | — | — | None |
| B | ♀ | 10 | None | — | — | None |
| I | ♀ | 50 | Sedation | 5 | 1 | Salivation (15 min) |
| J | ♀ | 50 | Sedation | 5 | >3 | Vomit |
| M | ♀ | 50 | None | — | — | None |
| N | ♀ | 50 | Sedation | 5 | 1 | Vomit (10–15 min) |
| 11 | ♀ | 100 | Sedation | 5 | 1 | Vomit (25–1Hr) |
| 0 | ♀ | 100 | Sedation | 5 | 1 | Vomit (5–25 min) |
| C | ♀ | 100 | Sedation | 5 | 1 | Vomit (20–45 min) |
| D | ♀ | 100 | Sedation | 5 | 1 | Vomit (10–20–45 min) |

Numbers in parenthesis indicate the times at which the side effect indicated was observed.

The concomitant administration of large doses (100 μg/kg) of Compound 1 and phenoperidine to a third group of animals (Table 11) induced no undesirable side effects but only a salutary combination of the neuroleptic's psychic indifference (manifested in the animals by the huddling position) and the sedation given by the analgesic.

TABLE II

Behavioral and Side Effects Elicited by the i.v. Administration of Compound 1 and Phenoperidine to Cebus Monkeys.

| Animal | Sex | Doses μg/kg Compound 1 -Phen. | Behavioral Changes | Onset Min | Duration Hr | Side Effects |
|---|---|---|---|---|---|---|
| 1 | | 100 + 100 | Huddle-Sedation | 5 | >5 | None |
| 2 | | 100 + 100 | Huddle-Sedation | 5 | >5 | None |
| 3 | | 100 + 100 | Huddle-Sedation | 5 | >5 | None |
| 4 | | 100 + 100 | Huddle-Sedation | 5 | >5 | None |

The compound of formula 1, or the combination thereof with a suitable analgesic agent, may be administered orally or parenterally, for instance, intramuscularly or intravenously, in combination with a pharmaceutically acceptable liquid or solid carrier. Advantageously, the compound or the combination is given parenterally; however, the method of administering the present active ingredients of this invention is not to be construed as limited to a particular mode of administration. The proportion of the Compound 1 or its combination with the analgesic agent is determined by its solubility in the given carrier, by the given carrier, by the chosen route of administration, and by standard biological practice. For parenteral administration to animals the compound of formula 1, or the combination, is dissolved or suspended in liquid carriers such as distilled water or oils of synthetic, animal petroleum or vegetable origin, for example, soy bean oil, sesame oil, mineral oil or propylene glycol. The parenteral formulation may also contain other solutes such as suspending agents, buffers or preservatives, as well as sufficient pharmaceutically acceptable salts or glucose to make the solution isotonic. The dosage will vary with the form of administration and with the particular species of animal to be treated and is preferably kept at 10 to 500 µg/kg, preferably 10 to 125 µg/kg, for the compound of formula 1 whether used alone or in combination with a suitable analgesic agent.

With reference to the combination, about one to 1000, preferably five to 100, parts by weight of the compounds of formula 1 is combined with one part by weight of the analgesic agent, although variations are possible depending on the potency of the analgesic. The weight-weight ratio is calculated on the basis of the free bases for the compound of formula 1 and the analgesic agent whether the latter is in the form of the free base or salt.

With reference to the use of the compound of formula 1, or of the combination in conjunction with an inhalation anasthetic, the compound or the combination is usually administered five minutes to four hours, preferably, 10 to 60 minutes, prior to the inhalation anesthetic.

From the present disclosure it will be apparent that the compound of formula 1 and the suitable analgesic agent can be utilized either in the form of their free base or in the form of a therapeutically acceptable salt. Accordingly, the present invention is not intended to be limited to the free base or the salt but to include both forms.

Finally, some definite advantages of the methods and formulation of this invention should be noted. More specifically, the compound of formula 1, and its combination with a suitable analgesic agent, have been found to have a quick onset of action and relatively short duration of activity, i.e. up to about four hours, allowing a rapid recovery period. Another advantage is that the compound of formula 1, alone or in combination with a suitable analgesic agent, has little or no effect on the cardiovascular system, in contrast to other neuroleptics available for NLA.

I claim:

1. A method for preventing painful conditions and providing psychic indifference to pain and stress in an animal subject comprising:
administering concomitantly or sequentially to said subject a neuroleptanalgesically effective dose comprising (+)(4a, 13b-trans)-(3-hydroxy,13b-trans)-3-isopropyl-2,3,4,4a,8,9,-13b,14-octahydro-11H-benzo[6,7]cyclohepta[1,2,3-de]pyrido[2,1-a]isoquinolin-3-ol, or
a therapeutically acceptable acid addition salt thereof, and less than a normally effective amount of a therapeutically acceptable analgesic agent or a therapeutically acceptable acid addition salt thereof, in a ratio ranging from 1 : 1 to 100:1 on a weight to weight basis, respectively.

2. The method of claim 1 followed five minutes to four hours thereafter by the administration to said subject of an anesthetically effective dose of a general anesthetic; said latter dose being substantially less than the anesthetically effective dose of the general anesthetic when given alone for the same purpose.

3. The method of claim 1 in which the ratio ranges from 5:1 to 100:1.

4. The method of claim 1 in which the dose comprises 10 to 500 µg/kg of (+)(4a,13b-trans)(3-hydroxy,13b-trans)-3-isopropyl-2,3,4,4a,8,9,13b,14-octahydro-1H-benzo[6,7]cyclohepta[1,2,3-de]pyrido[2,1-a]isoquinolin-3-ol, or a therapeutically acceptable acid salt thereof.

5. The method of claim 1 in which the dose comprises 10 to 125 µg/kg of (+)(4a,13b-trans)(3-hydroxy,13b-trans)-3-isopropyl-2,3,4,4a,8,9,13b,14-octahydro-1H-benzo[6,7]cyclohepta[1,2,3-de]pyrido(2,1-a]isoquinolin-3-ol, or a therapeutically acceptable acid addition salt thereof.

6. The method of claim 1 in which the therapeutically acceptable acid addition salt of (+)(4a,13b-trans)(3-hydroxy, 13b-trans)-3-isopropyl-2,3,4,4a,8,9,13b,14-octahydro-1H-benzo[6,7]cyclohepta[1,2,3-de]-pyrido[2,1-a]isoquinolin-3-ol is the corresponding hydrochloride and the analgesic agent is selected from the group consisting of fentanyl, meperidine, fentatienyl, azidomorphine, phenoperidine and dextromoramide.

7. The process of claim 2 in which the general anesthetic is halothane, nitrous oxide or a mixture of halothane and nitrous oxide.

8. A method for preventing painful conditions and providing psychic indifference to pain and stress in an animal subject comprising: administering parenterally to said subject 10 to 250 µg/kg of a neuroleptically effective dose of (+)(4a,13b-trans)-(3-hydroxy,13b-trans)-3-isopropyl-2,3,4,4a,8,9,13b,14-octahydro-1H-benzo[6,7]cyclohepta[1,2,3-de]pyrido[2,1-a]isoquinolin-3-ol, or a therapeutically acceptable salt thereof.

9. The method of claim 8 in which the therapeutically acceptable acid addition salt is the hydrochloride.

10. A method for preventing painful conditions and providing psychic indifference to pain and stress in an animal subject, comprising: administering parenterally to said subject 10 to 250 µg/kg of a neuroleptically effective dose of (+)(4a,13b-trans)-(3-hydroxy,13b-trans)-3-isopropyl-2,3,4,4a,8,9,13b,14-octahydro-1H-benzo[6,7]cyclohepta[1,2,3-de]pyrido[2,1-a]isoquinolin-3-ol, or a therapeutically acceptable salt thereof, followed 5 minutes to 4 hours thereafter by the administration to said subject of an anesthetically effective dose of a general anesthetic, said latter dose being substantially less than the anesthetically effective dose of the general anesthetic when given alone.

11. The process of claim 10 in which the general anesthetic is halothane, nitrous oxide or a mixture of halothane and nitrous oxide.

12. The method of claim 10 in which the therapeutically acceptable acid addition salt is the hydrochloride.

13. A pharmaceutical composition comprising (+)(4a,13b-trans)-(3-hydroxy,13b-trans)-3-isopropyl-2,3,4,4a,8,9,13b,14-octahydro-1H-benzo[6,7]Cyclohepta[1,2,3-de]pyrido[2,1-a]isoquinolin-3-ol, or a therapeutically acceptable acid addition salt thereof, and less than a normally effective amount of a therapeutically acceptable analgesic agent or a therapeutically acceptable acid addition salt thereof, in a ratio ranging from 1 : 1 to 1000:1 on a weight to weight basis, respectively, and a pharmaceutically acceptable carrier.

14. The pharmaceutical composition of claim 13 in which the ratio ranges from 5:1 to 100:1.

* * * * *

UNITED STATES PATENT AND TRADEMARK OFFICE
CERTIFICATE OF CORRECTION

PATENT NO. : 4,053,604
DATED : October 11, 1977
INVENTOR(S) : Jorge Jaramillo

It is certified that error appears in the above-identified patent and that said Letters Patent are hereby corrected as shown below:

Column 1, line 66, "along" should read --alone--.

Column 2, line 5, "droperidolfentanyl" should read --droperidol-fentanyl--.

Column 4, line 52, "assesses" should read --assessed--.

Column 5, line 13, "amount" should read --moment--.

Column 5, line 62, "αg/kg" should read --μg/kg--.

Column 6, line 17, "appliable" should read --applicable--.

Column 10, line 4, "means" should read --mean--.

Column 10, line 27, Table 8, "Students '+' test for paired data" should read --Students '†' test for paired data--.

Column 11, line 3, "mg/kg" should read --μg/kg--.

Claim 1, line 3, "subject" should read --subject,--.

UNITED STATES PATENT AND TRADEMARK OFFICE
CERTIFICATE OF CORRECTION

PATENT NO. : 4,053,604
DATED : October 11, 1977
INVENTOR(S) : Jorge Jaramillo

It is certified that error appears in the above-identified patent and that said Letters Patent are hereby corrected as shown below:

Claim 1, line 7, "11H" should read - -1H- -.

Claim 8, line 3, "subject" should read - -subject,- -.

Claim 13, line 3, "Cyclo" should read - -cyclo- -.

Signed and Sealed this

Fourth Day of July 1978

[SEAL]

Attest:

RUTH C. MASON
Attesting Officer

DONALD W. BANNER
Commissioner of Patents and Trademarks